United States Patent [19]

Urakami

[11] Patent Number: 5,344,768
[45] Date of Patent: Sep. 6, 1994

[54] PROCESS FOR THE PREPARATION OF PYRROLO-QUINOLINE QUINONE

[75] Inventor: Teizi Urakami, Niigata, Japan

[73] Assignee: Mitsubishi Gas Chemical Co., Inc., Tokyo, Japan

[21] Appl. No.: 91,884

[22] Filed: Jul. 14, 1993

Related U.S. Application Data

[63] Continuation of Ser. No. 819,572, Jan. 7, 1992, abandoned, which is a continuation of Ser. No. 442,429, Nov. 20, 1989, abandoned, which is a continuation of Ser. No. 852,195, Apr. 15, 1986, abandoned.

[30] Foreign Application Priority Data

Apr. 24, 1985 [JP] Japan ................................. 60-88255
Jul. 18, 1985 [JP] Japan ................................ 60-159238

[51] Int. Cl.$^5$ ...................... C12P 17/18; C12P 17/16; C12N 1/20
[52] U.S. Cl. ................................... 435/119; 435/118; 435/143; 435/252.1; 435/822; 435/824; 435/874
[58] Field of Search ............ 435/119, 118, 143, 252.1, 435/822, 824, 874

[56] References Cited

FOREIGN PATENT DOCUMENTS 0164943 12/1985 European Pat. Off. ............ 435/119

OTHER PUBLICATIONS

Urakami et al., *Int. S. Syst. Bact.* 1986, vol. 36, pp. 502–511.
Green et al., *Int. S. Syst. Bact.* 1988, vol. 38, pp. 124–127.
Ameyama et al, *Agric Biol Chem* vol. 48, pp. 561–565, 1984.
Patel et al, *Dev. Ind. Microbiol.* 1982, vol. 23, pp. 187–205.
de Beer et al, *Biochim. Biophys. Acta.* vol. 622, 1980, pp. 370–374.
Bergey's Manual 1974, pp. 268–269.
Bergeys Manual 1984, pp. 133–135.
Duine et al, *Biochim. Biophys Acta* vol. 524, 1978, pp. 277–287.
Duine et al. TIBS, vol. 6, pp. 278–280, 1981.

*Primary Examiner*—Irene Marx
*Attorney, Agent, or Firm*—Henry T. Burke

[57] ABSTRACT

Pyrrolo-quinoline quinone (PQQ) is microbiologically produced by culturing a bacterium in a medium containing methanol, methylamine or a mixture thereof as a carbon source and recovering PQQ from the culture medium. The bacteria are strains of *Methylobacterium, Ancylobacter, Hyphomicrobium, Xanthobacter, Thiobacillus, Microcyclus* and *Achromobacter*.

6 Claims, No Drawings

PROCESS FOR THE PREPARATION OF PYRROLO-QUINOLINE QUINONE

This application is a continuation of application Ser. No. 07/819,572 filed Jan. 7, 1992 which is a continuation of application Ser. No. 07/442,429 filed Nov. 20, 1989. The latter application is in turn, a continuation of application Ser. No. 06/852,195 filed Apr. 15, 1986. All of these applications are now abandoned.

The present invention relates to a process for preparing Pyrrolo-quinoline quinone, more particularly a process for microbiologically preparing the same by use of bacteria.

Pyrrolo-quinoline quinone (hereinafter abbreviated to "PQQ") is 2,7,9-tricarboxy-1H-pyrrolo[2,3-f]quinoline-4,5-dione having the formula

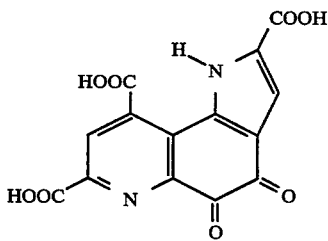

PQQ is purified and crystallized as coenzyme of methanol dehydrogenase produced from methanol-utilizing bacteria (S. A. Salisbury et al., Nature, Vol. 280, pp. 843–844, 1979). In recent years, PQQ is also found in such eucaryote as fungi and yeasts and mammals, as well as in bacteria. PQQ is considered to play an important role in a medical field, since it is coenzyme which facilitates enzymatic reactions or metabolism.

One of processes for producing PQQ is organic chemical synthesis (JACS. Vol. 103, pp. 5599–5600, 1981). However, the organic chemical synthesis is not economical, because the synthesis needs so many steps that it requires such a long time until synthesis is completed and, further, requires troublesome steps for removal of isomers and other various by-products. Furthermore, the yield of PQQ is not so high. Another is microbiological process has been described in Japanese published unexamined patent application 59-113896. However, the process is not economical, because yield is as low as $0.1-0.3\times10^{-8}$ mole/l (hereinafter referred to as "M"), i.e., 4–12 µg per liter.

The present inventor has been studying how to obtain PQQ by use of bacteria. The inventor has found that bacteria given below are capable of producing a large amount of PQQ: genus *Achromobacter, Methylobacillus, Methylomonas, Methanomonas, Protaminobacter, Methylobacterium, Protomonas, Mycoplana, Ancylobacter, Microcyclus, Hyphomicrobium, Xanthobacter, Thiobacillus, Alteromonas* or *Methylophaga*, or certain species belonging to genus *Pseudomonas*.

According to the present invention, a process for producing PQQ is provided wherein the bacterium defined below is cultured in a medium containing as a carbon source methanol, methylamine or mixtures thereof and then PQQ is recovered from the culture medium, i.e. the culture broth or a supernatant of the culture broth, said bacterium having capability of utilizing methanol and/or methylamine to produce PQQ and being selected from genus *Achromobacter, Methylobacillus, Methylomonas, Methanomonas, Protaminobacter, Methylobacterium, Protomonas, Mycoplana, Ancylobacter, Microcyclus, Hyphomicrobium, Xanthobacter, Thiobacillus, Alteromonas* or *Methylophaga*, or some species of genus *Pseudomonas*.

Any bacterium may be employed as long as it has capability of utilizing methanol and/or methylamine to produce a large amount of PQQ and belongs to genus *Achromobacter, Methylobacillus, Methylomonas, Methanomonas, Protaminobacter, Methylobacterium, Protomonas, Mycoplana, Ancylobacter, Microcyclus, Hyphomicrobium, Xanthobacter, Thiobacillus, Alteromonas* or *Methylophaga*, or some species of genus *Pseudomonas*. Examples of suitable bacteria are *Achromobacter methanophila* ATCC 21275 (=JCM 2841), ditto ATCC 21452 (=JCM 2842), ditto ATCC 21961 (=JCM 2843), *Methylobacillus glycogenes* ATCC 29475 (=JCM 2850=NCIB 11375), *Methylomonas methanolica* NRRL B-5458 (=JCM 2851), *Methylomonas thalassica* ATCC 33146, *Methylomonas clara* ATCC 31226 (=NCIB 11809), *Methanomonas methylovora* ATCC 21852 (=JCM 2840=NCIB 11376), ditto ATCC 21369 (=JCM 2844), ditto ATCC 21958 (=JCM 2847), ditto ATCC 21963 (=JCM 2848), *Methanomonas methylovora subsp. thianimophila* ATCC 21370 (=JCM 2849), *Protaminobacter candidus* ATCC 21372 (=JCM 2852), ditto ATCC 21959, *Protaminobacter thiaminophagus* ATCC 21371 (=JCM 2853), ditto ATCC 21926, ditto ATCC 21927, ditto ATCC 21957, ditto ATCC 21969, *Pseudomonas insueta* ATCC 21276 (=JCM 2854), ditto ATCC 21453 (=JCM 2855), ditto ATCC 21962 (=JCM 2856), ditto ATCC 21966, ditto ATCC 21967, *Pseudomonas methanolica* ATCC 21704 (=JCM 2857), ditto ATCC 21960 (=JCM 2858), ditto ATCC 21968, *Pseudomonas methylotropha* NCIB 10508 (=JCM 2859), ditto NCIB 10509, ditto NCIB 10510 (=JCM 2860), ditto NCIB 10511, ditto NCIB 10512 (=JCM 2861), ditto NCIB 10513, ditto NCIB 10514, ditto NCIB 10515, ditto NCIB 10592 (=JCM 2862), ditto NCIB 10593, ditto NCIB 10594 (=JCM 2863), ditto NCIB 10595, ditto NCIB 10596 (=JCM 2864), *Pseudomonas aminovorans* NCIB 9039, *Methylobacterium organophilum* ATCC 29983 (=NCIB 11278), *Protomonas extorquens* JCM 2802 (=DSM 1337=NCIB 9399), ditto JCM 2805 (=NCIB 9133=ATCC 14718=DSM 1338), ditto JCM 2806 (=DSM 1339=NCIB 9686), ditto JCM 2811 (=ATCC 14821), ditto JCM 2812 (=NCIB 10598), ditto JCM 2813 (=NCIB 10599), ditto JCM 2814 (=NCIB 10600), ditto JCM 2815 (=NCIB 10602), ditto JCM 2816 (=NCIB 10611), ditto JCM 2817 (=NCIB 10601), ditto JCM 2818 (=NCIB 10603), ditto JCM 2819 (=NCIB 10606), ditto JCM 2820 (=NCIB 10607), ditto JCM 2821 (=NCIB 10608), ditto JCM 2822 (=NCIB 10609), ditto JCM 2823 (=NCIB 10610), ditto JCM 2824 (=NCIB 10612), ditto JCM 2825 (=NCIB 10604), ditto JCM 2826 (=NCIB 10605), ditto JCM 2827 (=ATCC 21438), ditto JCM 2829 (=ATCC 29983=ICPB 4095), ditto JCM 2830 (=ATCC 27329=IAM 12099), ditto JCM 2831 (=IAM 12098), ditto JCM 2832 (names of *Protomonas extorquens* are based on International Journal of Systematic Bacteriology, Vol. 34, pp. 188–201, (1984)), *Mycoplanta rubra* NCIB 10409 (=JCM 2803), *Ancylobacter aquaticus* ATCC 25396 (=CCM 1786=DSM 101=NCIB 9721), ditto DSM 334, ditto ATCC 27068, ditto ATCC 27069 (names of *Ancylobacter aquaticus* are based on International Journal of Systematic Bacteriology, Vol. 33, pp.

397–398, (1983)) , *Microcyclus eburneus* ATCC 21373 (=DSM 1106), *Mycrocyclus polymorphum* NCIB 10516 (=DSM 2457), *Microcyclus methanolica* DSM 2666, ditto DSM 2667, ditto DSM 2668, ditto DSM 2669, *Hyphomicrobium variable* NCIB 10517, *Hyphomicrobium vulgare* NCIB 9698, ditto NCIB 9775, *Hyphomicrobium methylovorum* IFO 14180, *Hyphomicrobium sp.* DSM 1869, *Xanthobacter autotrophicus* DSM 432, ditto DSM 431, ditto DSM 597, ditto DSM 685, ditto DSM 1393, ditto DSM 1618, ditto DSM 2009, *Xanthobacter flavus* NCIB 10071 (=DSM 338), *Thiobacillus novellus* ATCC 8093 (=CCM 1077=DSM 506=IFO 12443=NCIB 9113), ditto NCIB 10456, *Thiobacillus versutus* ATCC 25364 (names of *Thiobacillus versutus* are based on International Journal of Systematic Bacteriology, Vol. 33, pp. 211–217, (1983)) , *Alteromonas thalassomethanolica* ATCC 33145, *Methylophaga marina* NCMB 2244 (=ATCC 35842), *Methylophaga thalassica* NCMB 2162, and *Methylophaga thalassica* NCMB 2163.

Variants obtained from the above strains may also be employed.

A medium employed has to contain as a carbon source methanol and/or methylamine ($CH_3NH_2$). Methylamine hydrochloride may be used as a source for methylamine. Concentrations of methanol and methylamine in the medium vary depending on bacteria employed. They are usually 3 wt. % or less, preferably 1.5 wt. % or less for methanol and 1 wt. % or less, preferably 0.5 wt. % or less for methylamine, on the basis of the medium, from a practical point of view. The medium further contains proper amounts of usual nitrogen sources and inorganic and/or organic salts. Ammonium sulfate, urea, ammonium nitrate, ammonium phosphate, peptone, meat extract, etc. are used as the nitrogen source. Phosphates, magnesium salts, iron salts, and, if necessary, a small amount of the other metal salts are used as the inorganic and/or organic salts. Furthermore, amino acid, nucleic acid, vitamine, yeast extract, malt extract and other growth promoting materials may be added. If the bacteria essentially require the nutrient, the medium has to contain necessary materials to this effect. Two to four wt. % of NaCl is added to the medium when the bacterium employed is *Methylomonas thalassica* ATCC 33146 or *Alteromonas thalassomethanolica* ATCC 33145, since these bacteria require NaCl for their growth. Instead, sea water may be used in place of NaCl and water for preparing the medium. The presence of $Na^+$ and/or $Mg^{++}$ is essential in the medium for genus *Methylophaga*, since all of the strains thereof mentioned above require $Na^+$ and $Mg^{++}$ for their growth. Preferable source for $Na^+$ is sea water, since the strains belonging to *Methylophaga* are marine bacteria. Instead, NaCl may be added to the medium until NaCl concentration is 2–4%.

Culturing conditions vary depending upon bacteria employed. All that is necessary, from a practical viewpoint, is to select a culturing temperature and pH of the culture broth within the usual ranges from 25° C. to 45° C. and of 6–8, respectively, taking into account of growth and propagation of bacteria employed. When the nitrogen source is an ammonium salt, in particular, pH of the medium becomes more acidic as bacteria propagate. Controlling pH of the culture broth is sometimes necessary by adding alkaline materials, for example, ammonia, caustic potash or caustic soda, in order to keep it at a constant level during the culturing. Ammonia is preferred. Culturing may be effected batchwise or continuously.

PQQ produced after the culturing is recovered by any means familiar to the skilled artisan. For instance, solid-liquid separation, for example, filtration and centrifugation, is applied to the culture broth in order to obtain supernatant by separation of cells from a culture broth. The supernatant and culture broth as it is before, for example, the filtration, which contains cells, may be used for the recovery. Recovery from the supernatant or the culture broth is effected, for example, by ion-exchange chromatography, gel-filtration of concentrate, solvent extraction of a dried product or affinity chromatography.

Identification of PQQ thus recovered is made by, for example, paper chromatography, thin-layer chromatography, elementary analysis, nuclear magnetic resonance spectrum, mass spectrometry, absorption spectra of UV, and high-performance liquid chromatography.

Quantitative analysis is made by use of a D-glucose dehydrogenase-activity deletion variant of *Pseudomonas aeruginosa* (Ameyama et al., FEBS Letters, Vol. 130, pp. 179–183, 1981) and *E. coli* (Ameyama et al., Agric. Biol. Chem., 49, pp. 1227–1231, 1985), absorption spectra of UV (Dekker et al., European Journal of Biochemistry Vol. 125, pp. 69–73 (1982)), or high-performance liquid chromatography.

The present invention is illustrated by the following examples.

EXAMPLE 1

An aqueous solution (200 ml, pH 7.1) each in which 3 g of $(NH_4)_2SO_4$, 1.4 g of $KH_2PO_4$, 2.1 g of $Na_2HPO_4$, 0.2 g of $MgSO_4 \cdot 7H_2O$, 30 mg of $CaCl_2 \cdot 2H_2O$, 30 mg of $FeC_6H_5O_7 \cdot XH_2O$, 5 mg of $MnCl_2 \cdot 4H_2O$, 5 mg of $ZnSO_4 \cdot 7H_2O$, 0.5 mg of $CuSO_4 \cdot 5H_2O$, 4 mg of thiamine hydrochloride, 4 mg of calcium pantothenate, 20 μg of biotin and 8 ml of methanol were dissolved in 1 l of water was poured into Erlenmeyer flasks (1 l each) and sterilized at 120° C. for 20 minutes. They were made main culturing mediums (hereinafter referred to as main medium).

Pre-culturing was made separately by culturing a bacterium given below each in the same main medium as above at 30° C. for 24 hours. The pre-cultured liquids were respectively inoculated in an amount of 1 vol. % to the main mediums. The liquids thus inoculated were subjected to culturing by rotary shakers at 30° C. Methanol concentrations in all of the culture broths were lowered to not more than 0.001 vol. % by two days cultivation. The supernatants were obtained by centrifugation of the culture broths, respectively. Amounts of PQQ in the supernatants are shown in Table 1.

TABLE 1

| Strains | Amount of PQQ (μg/l of supernatant) |
|---|---|
| *Achromobacter methanophila* ATCC 21275 | 73 |
| *Methylobacillus glycogenes* ATCC 29475 | 115 |
| *Methylomonas clara* ATCC 31226 | 160 |
| *Protaminobacter candidus* ATCC 21372 | 70 |
| *Protaminobacter thiaminophagus* ATCC 21371 | 80 |
| *Pseudomonas methanolica* ATCC 21704 | 140 |
| *Pseudomonas methylotropha* NCIB 10510 | 360 |
| *Methylobacterium organophilum* ATCC 29983 | 500 |
| *Protomonas extorquens* JCM 2802 | 750 |
| *Mycoplana rubra* NCIB 10409 | 600 |
| *Ancylobacter aquaticus* ATCC 25396 | 1000 |
| *Microcyclus eburneus* ATCC 21373 | 800 |
| *Microcyclus polymorphum* NCIB 10516 | 500 |
| *Microcyclus methanolica* DSM 2666 | 600 |
| *Hyphomicrobium variable* NCIB 10517 | 310 |

TABLE 1-continued

| Strains | Amount of PQQ (μg/l of supernatant) |
|---|---|
| Hyphomicrobium vulgare NCIB 9698 | 350 |
| Hyphomicrobium methylovorum IFO 14180 | 400 |
| Hyphomicrobium sp. DSM 1869 | 7000 |
| Xanthobacter autotrophicus DSM 432 | 1200 |
| Xanthobacter flavus NCIB 10071 | 1000 |
| Thiobacillus novellus NCIB 10456 | 2200 |
| Methanomonas methylovora ATCC 21852 | 400 |
| Methanomonas methylovora subsp. thiaminophila ATCC 21370 | 420 |
| Pseudomonas insueta ATCC 21276 | 340 |

EXAMPLE 2

An aqueous solution (200 ml, pH 7.1) each in which 3 g of $(NH_4)_2SO_4$, 1.4 g of $KH_2PO_4$, 2.1 g of $Na_2HPO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$ and 5 g of methylamine hydrochloride were dissolved in 1 l of water was poured into an Erlenmeyer flasks (1 l each) and sterilized at 120° C. for 20 minutes. They were made main mediums.

Pre-culturing was separately made by culturing *Thiobacillus versutus* ATCC 25364 and *Pseudomonas aminovorans* NCIB 9039, respectively, in the same main mediums as above at 30° C. for 24 hours. The pre-cultured liquids thus obtained were respectively inoculated in an amount of 1 vol. % to the main mediums. The liquids thus obtained were subjected to culturing by rotary shakers at 30° C. methylamine concentrations in all of the culture broths were lowered to not more than 0.01 vol. % by two days cultivation. The supernatants were obtained by centrifugation of the culture broths, respectively. Amounts of PQQ in the supernatants were 340 μg and 300 μg per liter, respectively.

EXAMPLE 3

An aqueous solution (200 ml, pH 7.1) each in which 3 g of $NH_4)_2SO4$, 1.4 g of $KH_2PO_4$, 2.1 g of $Na_2HPO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$, 0.2 g of yeast extract, 10 μg of vitamin $B_{12}$, and 8 ml of methanol were dissolved in 1 l of sea water was poured into Erlenmeyer flasks (1 l each) and sterilized at 120° C. for 20 minutes. They were made main mediums.

Pre-culturing was separately made by culturing bacterium given below each in the same main mediums as above at 30° C. for 24 hours. The pre-cultured liquids thus obtained were respectively inoculated in an amount of 1 vol. % to the main mediums. The liquids thus inoculated were subjected to culturing by rotary shakers at 30° C. Methanol concentrations in all of the culture broths were lowered to not more than 0.001 vol. % by two days cultivation. The supernatants were obtained by centrifugation of the culture broths, respectively. Amounts of PQQ therein are shown in Table 2.

TABLE 2

| Strains | Amount of PQQ (μg/l of supernatant) |
|---|---|
| Methylomonas thalassica ATCC 33146 | 2600 |

TABLE 2-continued

| Strains | Amount of PQQ (μg/l of supernatant) |
|---|---|
| Alteromonas thalassomethanolica ATCC 33145 | 6600 |

EXAMPLE 4

An aqueous solution (200 ml, pH 7.1) each in which 3 g of $(NH_4)_2SO_4$, 1.4 g of $KH_2PO_4$, 2.1 g of $Na_2HPO_4$, 0.2 g of $MgSO_4.7H_2O$, 30 mg of $CaCl_2.2H_2O$, 30 mg of $FeC_6H_5O_7.XH_2O$, 5 mg of $MnCl_2.4H_2O$, 5 mg of $ZnSO_4.7H_2O$, 0.5 mg of $CuSO_4.5H_2O$, 0.2 g of yeast extract, 10 μg of vitamin $B_{12}$ and 8 ml of methanol were dissolved in 1 l of sea water was poured into Erlenmeyer flasks (1 l each) and sterilized at 120° C. for 20 minutes. They were made main mediums.

Pre-culturing was separately made by culturing bacterium given below each in the same medium as above at 30° C. for 24 hours. The pre-cultured liquids were respectively inoculated in an amount of 1 vol. % to the main mediums. The liquids thus inoculated were subjected to culturing by rotary shakers at 30° C. Methanol concentrations in the culture broths were lowered to not more than 0.001 vol. % by one and a half days cultivation. The supernatants were obtained by centrifugation of the culture broths, respectively. Amounts of PQQ in the supernatants are shown in Table 3.

TABLE 3

| Strains | Amount of PQQ (μg/l of supernatant) |
|---|---|
| Methylophaga marina NCMB 2244 | 4400 |
| Methylophaga thalassica NCMB 2162 | 4000 |
| Methylophaga thalassica NCMB 2163 | 2600 |

EXAMPLE 5

Example 4 was repeated except that one liter of an aqueous NaCl solution containing 30 g of NaCl was used in place of the sea water. Methanol concentrations in all of the culture broths were lowered to not more than 0.001 vol. % by one and a half days cultivation. Amounts of PQQ are given in Table 4.

TABLE 4

| Strains | Amount of PQQ (μg/l of supernatant) |
|---|---|
| Methylophaga marina NCMB 2244 | 5000 |
| Methylophaga thalassica NCMB 2162 | 4600 |
| Methylophaga thalassica NCMB 2163 | 3000 |

EXAMPLE 6

Example 4 was repeated except that 5 g of methylamine hydrochloride per liter dissolved in sea water was used in place of the methanol. Methylamine concentrations in all of the culture broths were lowered to 0.01 vol. % at the end of the culturing. Amounts of PQQ are given in Table 5.

TABLE 5

| Strains | Amount of PQQ (μg/l of supernatant) |
|---|---|
| Methylophaga marina NCMB 2244 | 4200 |
| Methylophaga thalassica NCMB 2162 | 4100 |

TABLE 5-continued

| Strains | Amount of PQQ (μg/l of supernatant) |
|---|---|
| *Methylophaga thalassica* NCMB 2163 | 2800 |

EXAMPLE 7

Example 5 was repeated except that 5 g of methylamine hydrochloride per liter of the medium was used in place of the methanol. Methylamine concentrations in all of the culture broths were lowered to 0.01 vol. % at the end of the culturing. Amounts of PQQ are given in Table 6.

TABLE 6

| Strains | Amount of PQQ (μg/l of supernatant) |
|---|---|
| *Methylophaga marina* NCMB 2244 | 4100 |
| *Methylophaga thalassica* NCMB 2162 | 4300 |
| *Methylophaga thalassica* NCMB 2163 | 3000 |

According to the present invention, PQQ is able to obtain with lower cost and stably as disclosed above by use of bacteria.

I claim:

1. A process for the preparation of pyrroloquinoline quinone which comprises cultivating in a culture medium containing methanol as a carbon source a bacterial strain selected from the group consisting of:

*Methylobacterium organophilum* ATCC 29983
*Protomonas extorquens* JCM 2802
*Mycoplana rubra* NCIB 10409
*Ancylobacter aquaticus* ATCC 25396
*Microcyclus eburneus* ATCC 21373
*Microcyclus polymorphum* NCIB 10516
*Microcyclus methanolica* DSM 2666
*Hyphomicrobium variable* NCIB 10517
*Hyphomicrobium vulgare* NCIB 9698
*Hyphomicrobium methylovorum* IFO 14180
*Hyphomicrobium sp.* DSM 1869
*Xanthobacter autotrophicus* DSM 432
*Xanthobacter flavus* NCIB 10071
*Thiobacillus novellus* NCIB 10456
*Methanomonas methylovora* ATCC 21852
*Methanomonas methylovora* subsp. *thiaminophila* ATCC 21370
*Pseudomonas insueta* ATCC 21276
*Alteromonas thalassomethanolica* ATCC 33145
*Methylomonas thalassica* ATCC 33146
*Methylophaga marina* NCMB 2244
*Methylophaga thalassica* NCMB 2162
*Methylophaga thalassica* NCMB 2163
*Achromobacterr methanophila* ATCC 21275
*Methylobacillus glycogenes* ATCC 29475
*Methylomonas clara* ATCC 31226
*Protaminobacter candidus* ATCC 21372
*Protaminobacter thiaminophagus* ATCC 21371
*Pseudomonas methanolica* ATCC 21704 and
*Pseudomonas methylotropha* NCIB 10510 and recovering pyrroloquinoline quinone from the culture medium.

2. A process as in claim 1 wherein the bacterial strain is *Hyphomicrobium sp.* DSM 1869.

3. A process as in claim 1 wherein the bacterial strain is *Alteromonas thalassomethanolica* ATCC 33145.

4. A process as in claim 1 wherein the bacterial strain is *Methylophaga marina* NCMB 2244.

5. A process as in claim 1 wherein the bacterial strain is *Methylophaga thalassica* NCMB 2162.

6. A process as in claim 1 wherein the bacterial strain is *Methylophaga thalassica* NCMB 2163.

* * * * *